United States Patent [19]
Laufer

[11] Patent Number: 5,928,224
[45] Date of Patent: Jul. 27, 1999

[54] DEVICE FOR THE TREATMENT OF DAMAGED HEART VALVE LEAFLETS AND METHODS OF USING THE DEVICE

[75] Inventor: Michael D. Laufer, Menlo Park, Calif.

[73] Assignee: Hearten Medical, Inc., Tustin, Calif.

[21] Appl. No.: 08/789,375

[22] Filed: Jan. 24, 1997

[51] Int. Cl.$^6$ .................................................. A61B 17/36
[52] U.S. Cl. ................................ 606/27; 606/31; 606/41; 606/48; 607/101; 607/122
[58] Field of Search .................. 606/27–31, 41, 606/47, 48, 50, 8; 607/96, 98–102, 119, 122; 600/372, 373

[56] References Cited

U.S. PATENT DOCUMENTS

| | | | |
|---|---|---|---|
| 3,625,202 | 12/1971 | Oyoshirhara | 606/27 |
| 4,765,331 | 8/1988 | Petruzzi et al. | 128/303.14 |
| 4,949,718 | 8/1990 | Neuwirth et al. | 606/27 |
| 5,217,460 | 6/1993 | Knoepfler . | |
| 5,261,878 | 11/1993 | Galindo | 604/96 |
| 5,304,169 | 4/1994 | Sand | 606/5 |
| 5,364,389 | 11/1994 | Anderson | 606/27 |
| 5,437,664 | 8/1995 | Cohen et al. | 606/42 |
| 5,458,596 | 10/1995 | Lax et al. | 606/31 |
| 5,522,873 | 6/1996 | Jackman et al. | 607/122 |
| 5,527,313 | 6/1996 | Scott et al. | 606/41 |
| 5,529,067 | 6/1996 | Larsen et al. | 128/642 |
| 5,540,679 | 7/1996 | Fram et al. | 606/27 |
| 5,571,216 | 11/1996 | Anderson | 623/66 |
| 5,626,578 | 5/1997 | Tihon | 606/48 |
| 5,643,257 | 7/1997 | Cohen et al. | 606/48 |
| 5,673,695 | 10/1997 | McGee et al. | 128/642 |
| 5,707,369 | 1/1998 | Vaitekunas et al. | 606/27 |
| 5,738,683 | 4/1998 | Osypka | 606/47 |
| 5,823,956 | 10/1998 | Roth et al. | 600/374 |

*Primary Examiner*—Danton D. DeMille
*Assistant Examiner*—David M. Ruddy
*Attorney, Agent, or Firm*—Burns, Doane, Swecker & Mathis, LLP

[57] ABSTRACT

A device and method for treating infected or damaged heart valve tissue by selectively heating, applying pressure, or both to the heart valve tissue to sterilize any infected portion of the tissue, reshape any misshapen portion, effect selective thinning of any thickened portion, and reduce the floppiness of any selected portion. The heat can be applied to or induced in the heart valve tissue.

15 Claims, 5 Drawing Sheets

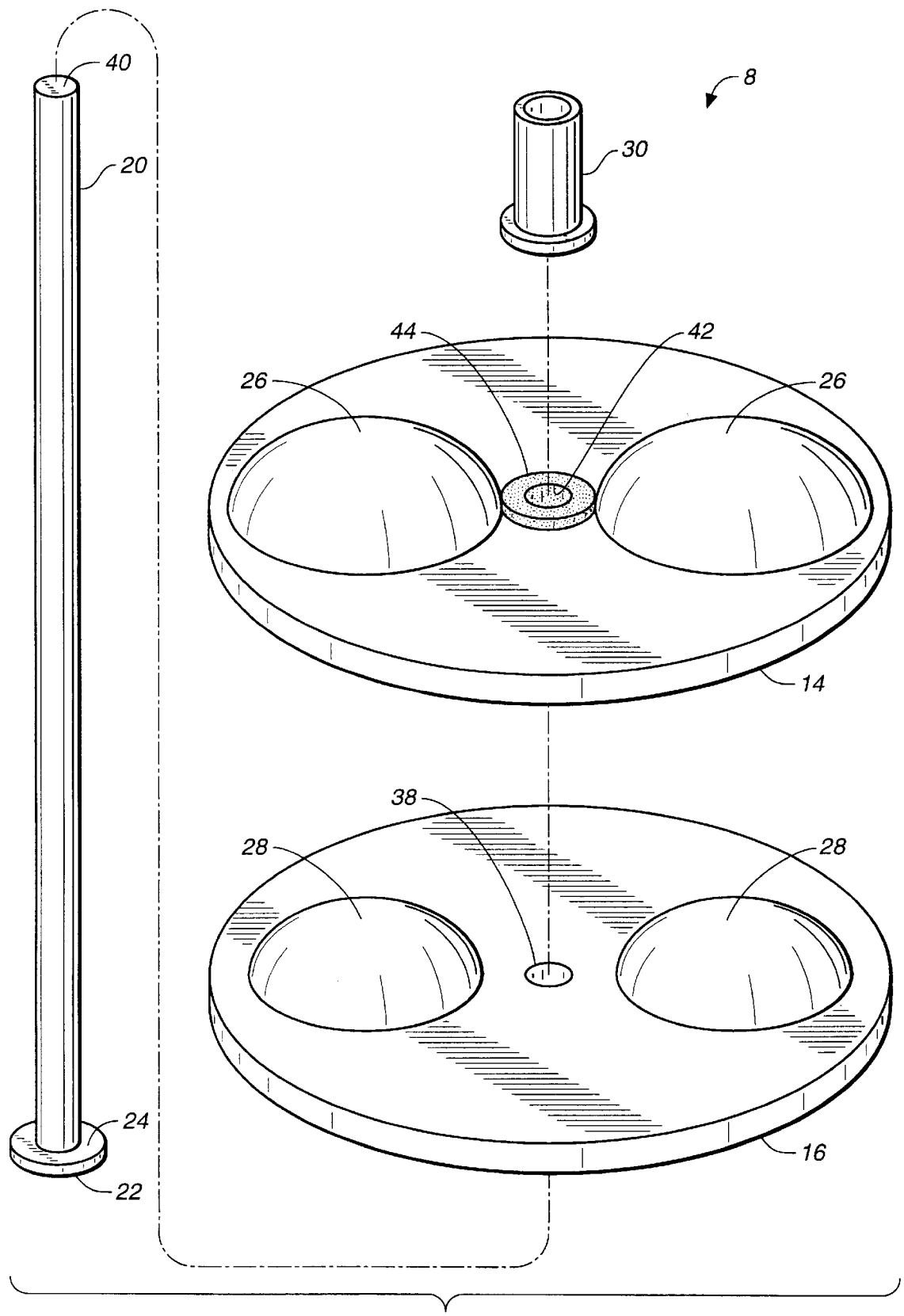
FIG._1

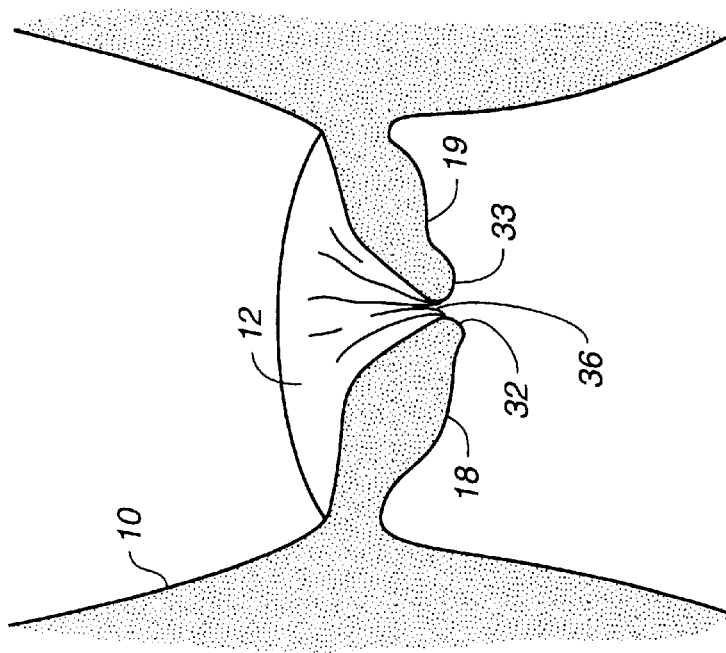
FIG._3
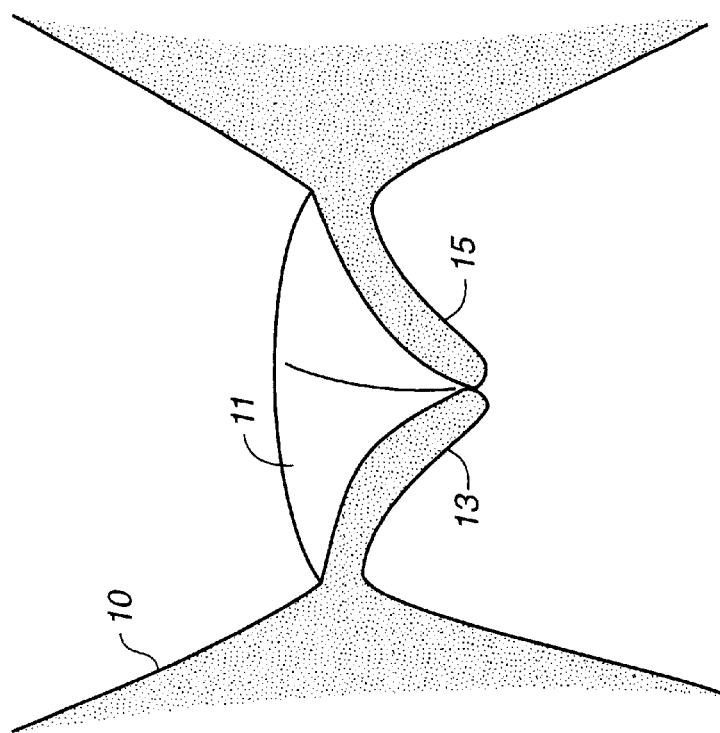
FIG._2

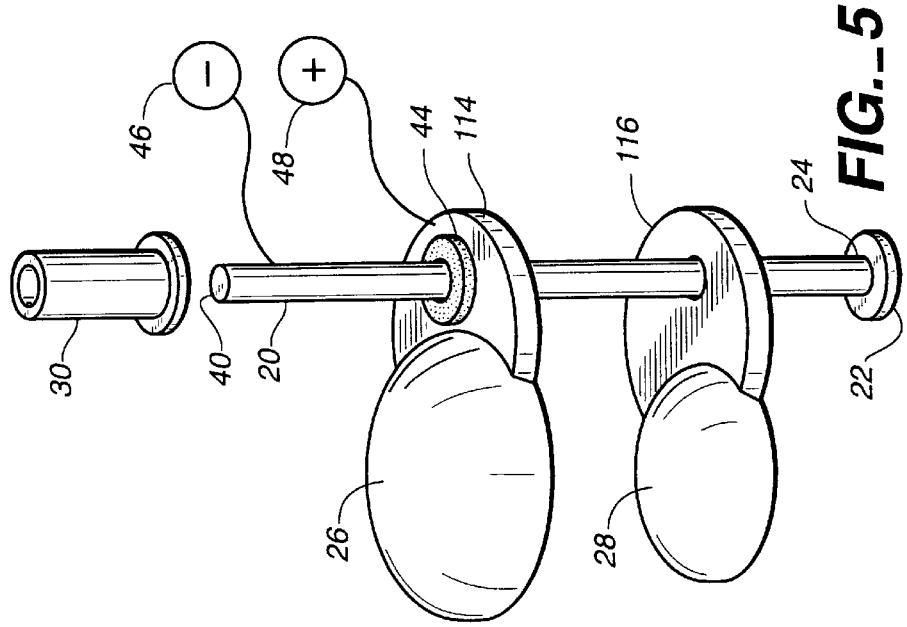
FIG._5
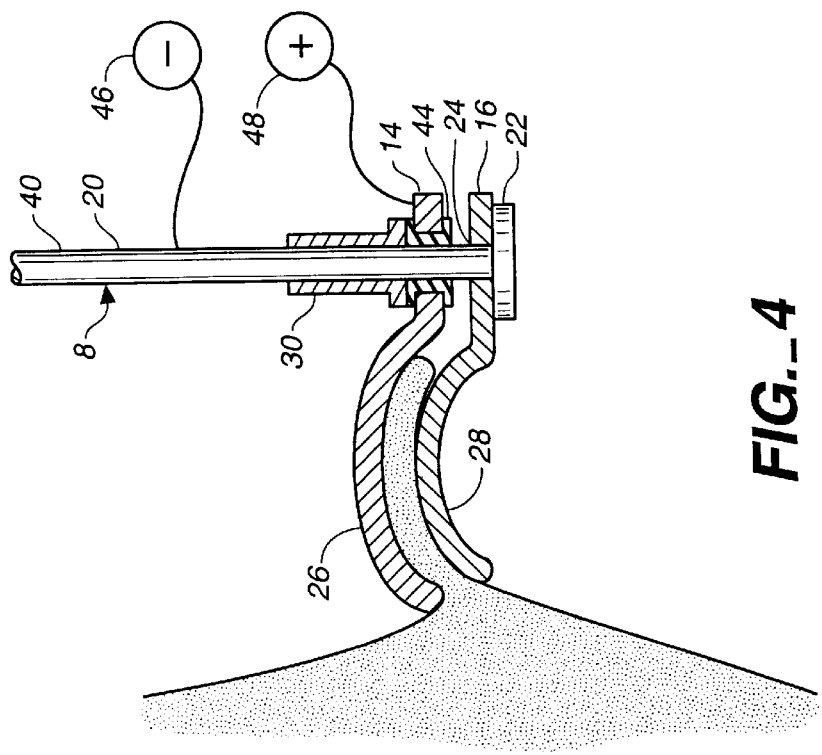
FIG._4

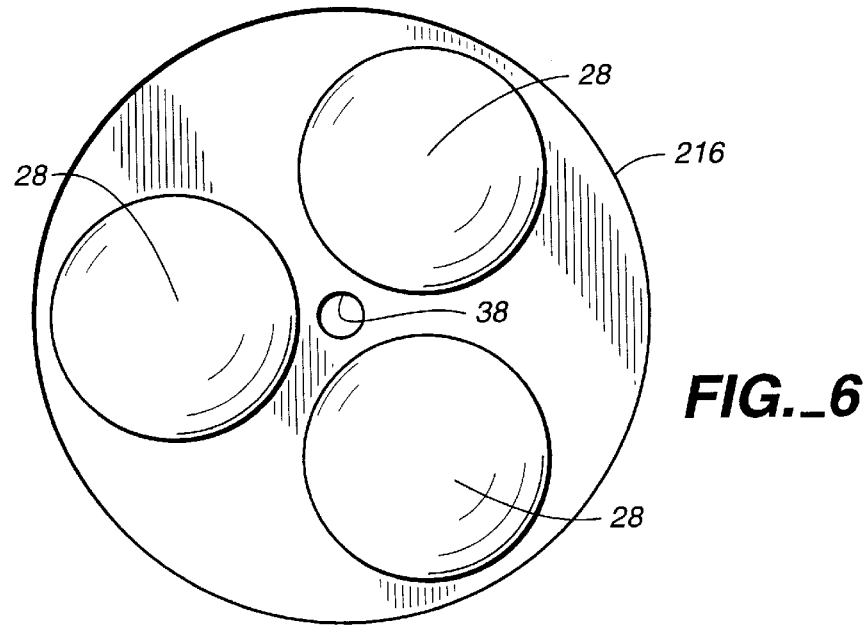
FIG._6
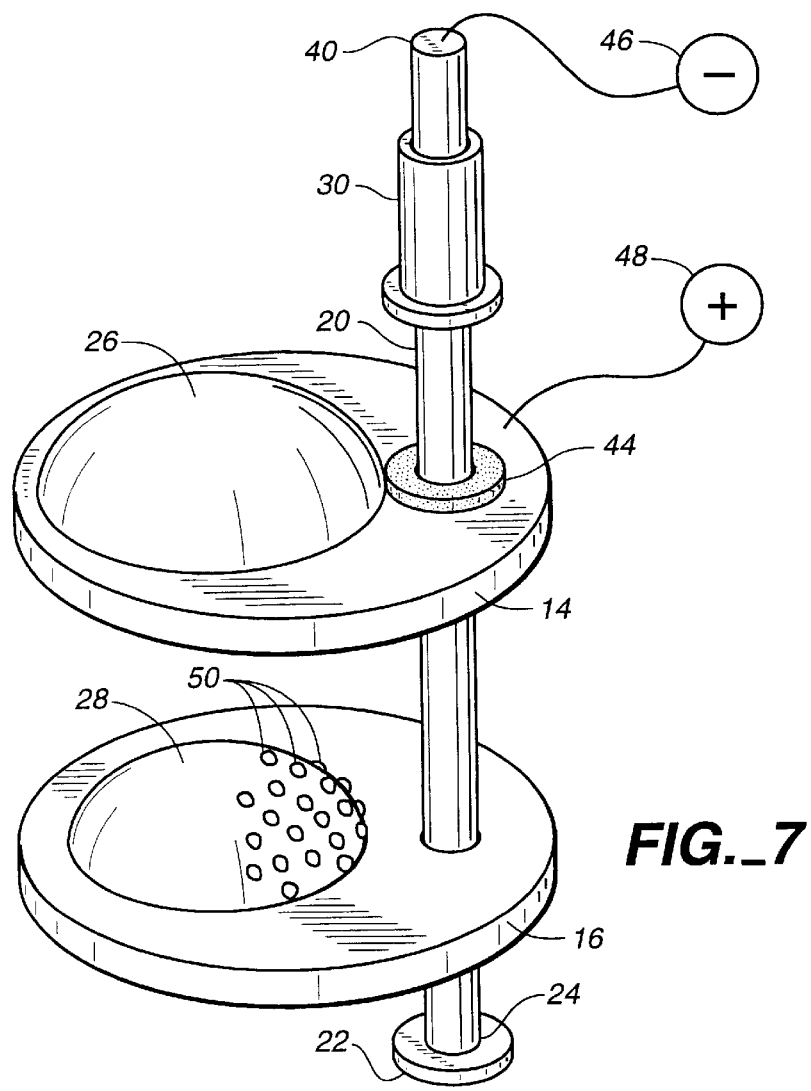
FIG._7

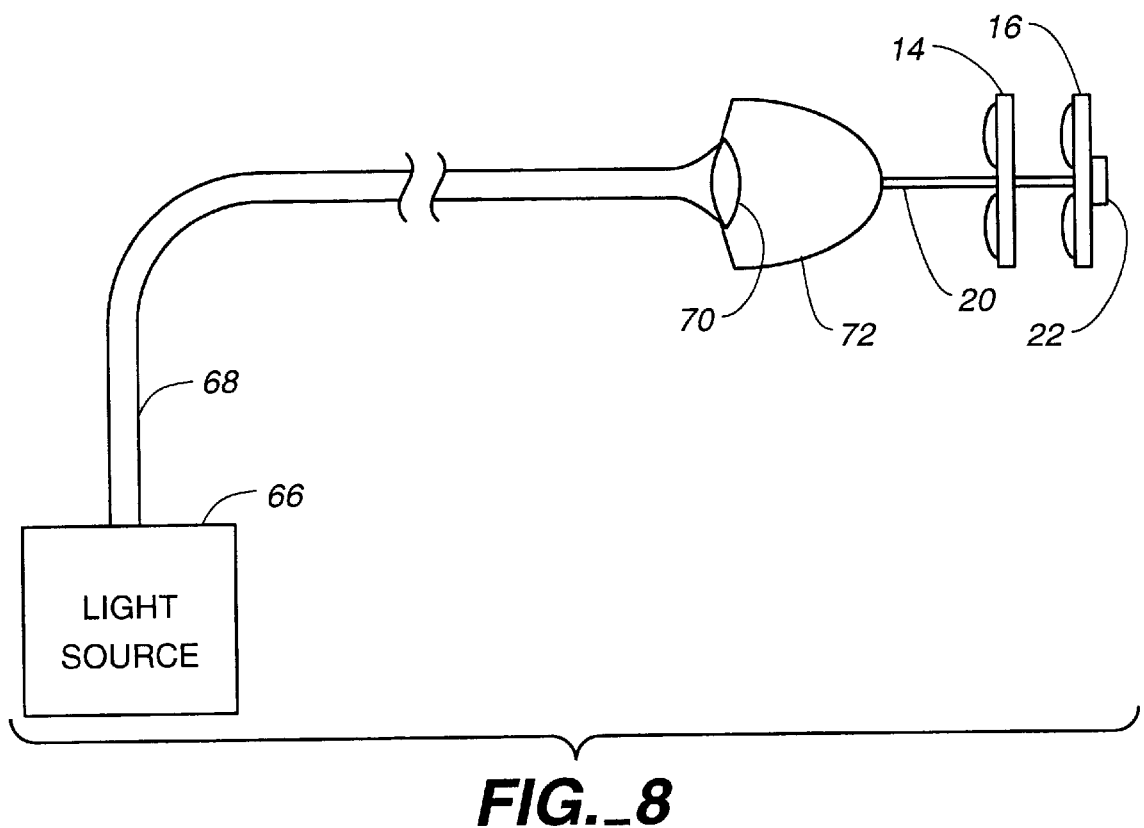
FIG._8

DEVICE FOR THE TREATMENT OF DAMAGED HEART VALVE LEAFLETS AND METHODS OF USING THE DEVICE

FIELD OF THE INVENTION

The present invention is related generally to the modification of heart tissue for the treatment of damaged heart valve leaflets.

BACKGROUND OF THE INVENTION

As is well known, the heart has four chambers for receiving and pumping blood to various parts of the body. During normal operation of the heart, oxygen-poor blood returning from the body enters the right atrium. The right atrium fills with blood and eventually contracts to expel the blood through the tricuspid valve to the right ventricle. Contraction of the right ventricle ejects the blood in a pulse-like manner into the pulmonary artery and each lung. The oxygenated blood leaves the lungs through the pulmonary veins and fills the left atrium. The left atrium fills with blood and eventually contracts to expel the blood through the mitral valve to the left ventricle. Contraction of the left ventricle forces blood through the aorta to eventually deliver the oxygenated blood to the rest of the body.

There are conditions in which the heart valves (i.e., mitral valve, aortic valve, pulmonic value and tricuspid valve) do not close completely (i.e., incompetence) causing reverse flow of blood through the valve (i.e., regurgitation) resulting in a murmur as blood goes back through the valve. Often times, the valve leaflets are found to have been damaged by infection (e.g., streptococcus). The valve leaflets damaged by infection are typically thickened, especially on the edges, therefore incapable of sealing the opening across which they lie.

Other times, the valve leaflets are found to be atherosclerotic (i.e., thickened and calcified). Typical treatments for atherosclerosis include inflating a balloon in the valve to break plaque loose from the valve and, for severe cases, valve replacement with either a mechanical or pig valve. There are some conditions in which the valve leaflets show indication of subacute bacterial endocarditis. Typically, a valve replacement procedure is conducted to treat subacute bacterial endocarditis.

Collagen-containing tissue is ubiquitous in the human body and demonstrates several unique characteristics not found in other tissues. Intermolecular cross links provide collagen-containing tissue with unique physical properties of high tensile strength and substantial elasticity. A property of collagen is that its material properties can be changed when elevated in temperature and force is applied. The molecular response to temperature elevation and force is believed to be the result of rupture of the collagen stabilizing cross links or the result of a change in the hydration of the tissue.

There has been discussion in the existing literature regarding alteration of collagen-containing tissue in different parts of the body. One known technique for effective use of this knowledge of the properties of collagen is through the use of infrared laser energy to effect tissue heating. The use of infrared laser energy as a corneal collagen shrinking tool of the eye has been described and relates to laser keratoplasty, as set forth in U.S. Pat. No. 4,976,709. The importance of controlling the localization, timing and intensity of laser energy delivery is recognized as paramount in providing the desired soft tissue shrinkage affects without creating excessive damage to the surrounding non-target tissues. Another known technique of altering collagen is described in U.S. Pat. No. 5,458,596 to treat joints. U.S. Pat. No. 5,437,664 describes using a catheter for venous occlusion and coagulation of blood.

SUMMARY OF THE INVENTION

The present invention provides a device and method for treating damaged heart valve leaflets of a mammalian heart by heating or compressing, or both, the valve leaflet to sterilize any infected portion of the leaflet, reshape any misshapen portion, effect selective thinning of any thickened portion, or reduce the floppiness of any selected portion.

In one aspect of the invention, there is provided an apparatus for treating an infected or damaged heart valve leaflet, having a support rod having a first end, a first member having at least one protrusion thereon and a first member opening through the first member for receiving the support rod, the first member being adjacent the first end of the support rod, a second member having at least one protrusion thereon corresponding to the protrusion on the first member and a second member opening through the second member for receiving the support rod, and means for energizing the first member and the second member to heat the infected or damaged heart valve leaflet.

In another aspect of the invention, there is provided a method for treating an infected or damaged heart valve leaflet, including the steps of placing a member in contact with the heart valve leaflet and energizing the member to heat the heart valve leaflet to a temperature sufficient to sterilize or reshape the heart valve leaflet.

In another aspect of the invention, there is provided a method for treating an infected or damaged heart valve leaflet, including the steps of placing a first member having at least one curved surface thereon in contact with a first side of the heart valve leaflet such that the heart valve leaflet conforms to the curved surface, placing a second member having at least one curved surface thereon in contact with a second side of the heart valve leaflet such that the heart valve leaflet is in contact with the curved surface on the first member and the curved surface on the second member, and energizing the first member and the second member to heat the heart valve leaflet to a temperature sufficient to sterilize or reshape the heart valve leaflet.

In yet another aspect of the invention, there is provided a method for training a person to perform a method for treating an infected or damaged heart valve leaflet, including the step of demonstrating or instructing the performance of the following steps of placing a first member having at least one protrusion thereon in contact with a first side of the heart valve leaflet such that the heart valve leaflet conforms to the surface of the protrusion, placing a second member having at least one protrusion thereon in contact with a second side of the heart valve leaflet such that the heart valve leaflet is in contact with the protrusion on the first member and the protrusion on the second member, and energizing the first member and the second member to heat the heart valve leaflet to a temperature sufficient to sterilize or reshape the heart valve leaflet.

In still another aspect of the invention, there is provided a modified mammalian heart having a heated heart valve leaflet which has been sterilized or reshaped.

In yet still another aspect of the invention, there is provided a method for treating an infected heart valve leaflet, including the step of energizing a heating element in contact with or close proximity to the infected heart valve leaflet to raise the temperature of an infected region to a temperature sufficient to sterilize the heart valve leaflet.

In another aspect of the invention, there is provided a method for training a person to perform a method for treating an infected or damaged heart valve leaflet, including the step of demonstrating or instructing the performance of the following steps of placing a member in contact with the heart valve leaflet, and energizing the member to heat the heart valve leaflet to a temperature sufficient to sterilize or reshape the heart valve leaflet.

In another aspect of the invention, there is provided a modified mammalian heart having a compressed heart valve leaflet which has been reshaped.

BRIEF DESCRIPTION OF THE DRAWINGS

As used herein, like reference numerals will designate similar elements in the various embodiments of the present invention wherein:

FIG. 1 is an exploded perspective view of one embodiment of a device for treating damaged or infected heart valve leaflets;

FIG. 2 is a mammalian heart with a healthy heart valve;

FIG. 3 is a mammalian heart with a damaged or infected heart valve;

FIG. 4 is an enlarged diagrammatic representation partially in cross-section of a portion of the device during to treatment of the damaged valve leaflet;

FIG. 5 is another embodiment of the device in accordance with the present invention;

FIG. 6 is still another embodiment of a portion of the device in accordance with the present invention;

FIG. 7 is yet another embodiment of the device in accordance with the present invention; and FIG. 8 is a diagrammatic representation of yet still another embodiment of the device in accordance with the present invention.

DETAILED DESCRIPTION OF THE PREFERRED EMBODIMENTS

The present invention provides a device and method for altering the material properties of collagen-containing damaged or infected heart valve tissue in a mammalian heart. There also is provided a method of training a person to perform a method for treating the damaged or infected heart valve tissue in a mammalian heart. The invention accurately controls the inducement of heat or application of heat within a specific thermal range, and delivers thermal energy to the damaged or infected valve leaflet tissue to sterilize any infected portion of the tissue, reshape any misshapen portion, effect selective thinning of any thickened portion, or reduce the floppiness of any selected portion. The invention compresses the damaged valve leaflet tissue in some instances to reshape the leaflet. As a result, the competency of the damaged or infected heart valve is restored. Likewise, a modified mammalian heart having a heated, reshaped heart valve leaflet results.

FIG. 1 illustrates the components of the device 8 in accordance with a first embodiment of the present invention. The device 8 comprises a rod 20 having a stop plate 22 at a distal end 24 of the rod and two plates 14 and 16 for applying heat (or inducing heat in) to damaged or infected heart valve leaflets 18 and 19 (FIG. 3). The top plate 14 and bottom plate 16 have mating protrusions 26 and 28, respectively, for contacting respective surfaces of the valve leaflets 18 and 19 being treated as described below. A releasable locking member 30 is also provided to apply pressure and hold the plates 14 and 16 in compression on the valve leaflets 18 and 19 being treated, if it is desired to heat and compress the valve leaflets. Therefore, it will be appreciated that the valve leaflets can be treated with heat, compression, or both in accordance with the present invention.

Referring to FIG. 2, there is illustrated a heart 10 having a healthy heart valve 11 which is a mitral or bicuspid valve having two valve leaflets 13 and 15 which meet and close off completely during operation. The heart valve 12 of FIG. 3 is a damaged or infected mitral or bicuspid valve having two valve leaflets 18 and 19. As best seen in FIG. 3, the edges 32 and 33 of leaflets 18 and 19, respectively, are thickened and jagged due to either current or past infection or atherosclerosis. As a result, the valve 12 is incompetent such that the edges 32 of leaflet 18 do not seal with the edges 33 of leaflet 19 when the valve 12 closes. In some circumstances, leaflet 18 may have a creased portion that results in the leaflet being inverted partially from its normal convex or domed shape. The present invention can be used to treat one or both of these conditions, if present, in the damaged or infected mitral valve 12. The present invention can be used with the tricuspid, pulmonic or aortic valves, as well, as will be discussed in more detail below.

The valve 12 of the heart 10 can be accessed with conventional open chest surgery techniques. A top plate 14 and bottom plate 16 are placed on opposite sides of the valve 12 to induce resistive heating in the heart valve tissue when energy is applied across the plates 14 and 16 (FIG. 4). The bottom plate 16 is placed below the valve 12 by a surgeon (or an individual demonstrating) by inserting the distal end 24 of the rod 20 through the opening 36 between the valve leaflets 18 and 19, then placing the bottom plate 16 onto the rod 20 through the opening 38 in the bottom plate 16. (Likewise, an individual can instruct a surgeon on how to accomplish the method of the present invention with the device 8 or other embodiments disclosed herein.) The bottom plate 16 is pushed down on the rod 20 and worked through the opening 36 between the valve leaflets 18 and 19. The bottom plate 16 rests in contact with the stop plate 22 at the distal end 24 of the rod 20. The rod 20 is pulled back up slightly until the protrusions 28 on bottom plate 16 contact the bottom surfaces of each of the valve leaflets (only one shown in FIG. 4). The protrusion 28 on the bottom plate 16 pushes up on valve leaflet 18 to return the leaflet to its normal convex or domed shape. Top plate 14 is placed above the valve 12 by inserting the proximal end 40 of the rod 20 through the opening 42 in the top plate 14. The top plate 14 is pushed down on the rod 20 into contact with the top surface of each of the valve leaflets. The concave portion of the protrusions 26 on top plate 14 mate with the convex portion of the protrusions 28 on bottom plate 16. The top plate 14 is electrically insulated from the rod 20 by insulating disk 44. A negative electrode 46 is attached to the proximal end 40 of the rod 20. The bottom plate 16 is in electrical communication with the rod 20. A positive electrode 48 is attached to the top plate 14 such that the top plate 14 and bottom plate 16 operate as electrodes. The positive and negative electrodes 48 and 46 are then energized by the surgeon to function as a heating element. As the electrodes are energized the temperature of the tissue in the desired valve leaflet 18 and/or 19 is raised to a temperature sufficient to sterilize or reshape the valve leaflet(s) without ablating the tissue or damaging the healthy tissue surrounding the valve 12. The term "heating element" as used herein encompasses elements that apply energy thereby inducing heat in the tissue as well as to elements that apply heat to the tissue. In a preferred embodiment, the tissue is heated to a temperature in the range of about 40 degrees Celsius to about 110 degrees Celsius, more preferably about 60 degrees Celsius to about 65 degrees Celsius.

If compression is needed for treatment, either with or without heat, a releasable locking member 30 (FIGS. 1 and 4) is pushed down on the rod 20 into contact with the top plate 14 to apply pressure to the valve leaflets 18 and 19 located between the convex portion of the protrusions 28 on bottom plate 16 and the concave portion of the protrusions 26 on the top plate 14 (FIG. 4). The amount of applied pressure depends on the condition of the valve leaflet. Typically, the applied pressure is between 1 and 50 pounds per square inch. The releasable locking member 30 is electrically insulated from the rod 20 and the top plate 14. After the desired treatment area has been heated (and compressed if needed), it is allowed to cool. Energy is no longer applied after there has been sufficient sterilization or reshaping of the valve tissue to restore valve competency. Likewise, pressure is no longer applied after there has been sufficient reshaping of the valve tissue to restore valve competency if no heating is needed. Sufficient sterilization or reshaping may be detected visually, mechanically, or with appropriate feed back variables, such as temperature monitoring, or any other suitable method.

The convex portion of the protrusions 28 on bottom plate 16 and the concave portion of the protrusions 26 on the top plate 14 are shaped to contact the valve leaflets 18 and 19 in a desired manner so that the valve leaflets 18 and 19 are thinned and smoothed out at the edges 32 and 33, respectively, to restore competency to the heart valve 12. The convexity and concavity of the protrusions 26 and 28, along with the temperature and/or pressure, control the reshaping of the valve leaflets. As can be seen in FIG. 7, an alternate embodiment of top plate 14 and bottom plate 16 can have protrusions 50, bumps, scales, ridges, grooves, indentations, or the like on their respective surfaces that contact the valve leaflets to prevent movement of the leaflets. A series of differently shaped and/or sized protrusions and plates can be used to treat the valve leaflets 18 and 19 incrementally until the desired shape or competency is reached.

Some examples of different plates are shown in FIGS. 5 and 6. In FIG. 5, the top plate 114 and bottom plate 116 are basically only one-half of the top plate 14 and bottom plate 16 shown in FIG. 1. In this way, the rod 20 and bottom plate 116 can be more easily inserted through the valve 12. The top plate 114 and bottom plate 116 are used to treat either valve leaflet 18 or 19 whichever may be infected or damaged. If both leaflets are damaged, one leaflet can be treated first then the top plate 114 and bottom plate 116 can be rotated to treat the other leaflet. As will be evident to one of ordinary skill in the art, a tricuspid valve can be treated with the top plate 114 and bottom plate 116 of FIG. 5 by treating each infected or damaged valve leaflet in the tricuspid valve separately. In FIG. 6, there is shown a bottom plate 216 having three protrusions 28 for treating a tricuspid valve (not shown) in combination with a top plate (not shown) having three protrusions (not shown) for mating with the protrusions 28 on plate 216.

The device 8 illustrated in the figures utilizes resistive heating of the valve tissue, but it is also within the scope of the invention that other means can be utilized. The method is contemplated to be used with any suitable appliance for applying radiant energy, thermal energy, or to otherwise heat the infected or damaged tissue. For example, a radio-frequency generator connected to the top plate 14 and 16 in a bipolar manner (diagrammatically similar to the resistive heating embodiment) can be used. A unipolar configuration can be used as well. An outer electrode (not shown) having a much larger surface area than the plates 14 and 16 is placed on the outer surface of the patient's body. For example, an external metal mesh or solid plate is placed on the skin. Both the plates and the outer electrode are connected to radio-frequency generator which produces an electric field at a high frequency within the patient's body. Because the surface area between the plates 14 and 16 is much smaller than the surface area of the outer electrode, the density of the high frequency electric field is much higher between the plates. The electric field reaches its highest density between the plates. The increased density of the field between the plates produces localized heating of the valve leaflet tissue. In either embodiment, when the top plate 14 and 16 are positioned at the desired treatment site, the radio-frequency generator is activated to provide suitable energy, preferably at a selected frequency in the range of 10 megahertz to 1000 megahertz, to heat the leaflet tissue to a temperature sufficient to sterilize or reshape the leaflet tissue without damaging the healthy tissue surrounding the heart valve 12. Preferably, the emitted energy is converted within the leaflet tissue into heat in the range of about 40 degrees Celsius to about 110 degrees Celsius, more preferably in the range of about 60 degrees Celsius to about 65 degrees Celsius and in the range of about 100 degrees Celsius to about 110 degrees Celsius for sterilization. The radio-frequency energy is preferably applied at low power levels (e.g., 1 to 20 watts/cm$^2$). Suitable radio-frequency power sources are readily commercially available. In one embodiment, the radio-frequency generator has a single channel, delivering approximately 1 to 20 watts/cm$^2$ of energy and possessing continuous delivery capability.

FIG. 8 is a diagrammatic representation of another embodiment of the present invention wherein the top plate 14 and bottom plate 16 are heated with a light source 66, for example, a laser or halogen source. The light source 66 transmits light via fiber optic light pipe 68 to lens 70 which diffuses the light onto parabolic heat sink 72 to convert the light energy to heat that is conducted through the rod 20 to the top plate 14 and bottom 16.

The heating element of any of the embodiments can be made to provide protection against overheating of the valve tissue. Techniques, for example temperature monitoring or electrical characteristic monitoring (e.g., impedance), can be utilized in a system which shuts down the application of energy to the heating element to avoid ablating the tissue or damaging healthy tissue. The surgeon can, if desired, override the feedback control system. A microprocessor can be included and incorporated into the feedback control system to switch the power on and off, as well as modulate the power. The microprocessor can serve as a controller to watch the temperature and modulate the power in order to avoid over-heating of the tissue. Furthermore, the system can include auditory or visual feedback indicators for signalling when reshaping, heating, temperature, or other variables are occurring and also when any have reached or exceeded desired conditions.

It is to be understood that other forms of energy, in addition to those discussed above and diagrammatically similar as those discussed, such as light, microwaves, ultrasound, and the like can be used to apply or induce heat in the desired tissue, and that the thermal energy generated from a hot fluid element (e.g., liquids, gases, combinations of liquids and gases, etc.), a curie point element, or similar elements can be used as well. The plates in accordance with any of the embodiments can be a number of different materials including but not limited to conductive polymer, stainless steel, platinum, or other noble metals.

While several particular embodiments of the invention have been illustrated and described, it will be apparent that various modifications can be made without departing from the spirit and scope of the invention. Accordingly, it is not intended that the invention be limited, except as by the appended claims.

What is claimed is:

1. An apparatus for treating an infected or damaged heart valve leaflet, comprising:

a support rod having a first end;

a first member having at least one protrusion with at least one convex surface thereon and a first member opening through the first member for receiving the support rod, the first member being adjacent the first end of the support rod;

a second member having at least one protrusion with at least one concave surface thereon corresponding to the protrusion on the first member and wherein the concave surface mates with the corresponding convex surface to form a shape of a normal heart valve leaflet, and a second member opening through the second member for receiving the support rod; and means for energizing the first member and the second member to heat the infected or damaged heart valve leaflet.

2. The apparatus of claim 1 wherein the first member and the second member comprise electrodes for heating the heart valve leaflet.

3. The apparatus of claim 1 wherein the means for energizing comprises a radio-frequency generator.

4. The apparatus of claim 1 wherein the means for energizing comprises microwave means for heating the heart valve leaflet.

5. The apparatus of claim 1 wherein the means for energizing comprises ultrasound means for heating the heart valve leaflet.

6. The apparatus of claim 1 wherein the means for energizing comprises light means for heating the heart valve leaflet.

7. The apparatus of claim 1 wherein the means for energizing comprises a hot fluid element.

8. The apparatus of claim 1 further comprising a feedback indicator.

9. The apparatus of claim 8 wherein the feedback indicator is an auditory signal.

10. The apparatus of claim 8 wherein the feedback indicator is a visual signal.

11. The apparatus of claim 8 wherein the feedback indicator is indicative of temperature.

12. The apparatus of claim 8 wherein the feedback indicator is indicative of electrical characteristics.

13. The apparatus of claim 1 further comprising a member for applying pressure with the first member and the second member to the heart valve leaflet.

14. The apparatus of claim 1 wherein the first member has a plurality of protrusions thereon and the second member has a plurality of protrusions thereon corresponding to the plurality of protrusions on the first member.

15. The apparatus of claim 1 wherein the protrusion on the first member has a plurality of protrusions or indentations thereon.

* * * * *